United States Patent [19]

Hoda et al.

[11] Patent Number: 4,830,503
[45] Date of Patent: May 16, 1989

[54] REFLECTION DENSITY MEASURING SYSTEM

[75] Inventors: Yoshihiko Hoda; Nobuhiko Ogura, both of Kanagawa, Japan

[73] Assignee: Fuji Photo Film Co., Ltd., Kanagawa, Japan

[21] Appl. No.: 39,124

[22] Filed: Apr. 16, 1987

[30] Foreign Application Priority Data

Apr. 16, 1986 [JP] Japan .................. 61-87708
Apr. 16, 1986 [JP] Japan .................. 61-87709

[51] Int. Cl.⁴ .............................. G01N 21/47
[52] U.S. Cl. .............................. 356/446
[58] Field of Search ............. 356/73.1, 445, 446; 250/227; 350/96.15, 96.26

[56] References Cited

U.S. PATENT DOCUMENTS

| | | | |
|---|---|---|---|
| 3,392,623 | 10/1964 | Walker et al. | 356/445 X |
| 3,801,181 | 4/1974 | Kitano et al. | 350/96.26 X |
| 3,806,256 | 4/1974 | Ishak | 356/446 |
| 4,009,382 | 2/1977 | Nath | 350/96.26 X |
| 4,408,495 | 10/1983 | Couch et al. | 250/227 X |
| 4,464,054 | 8/1984 | Karras et al. | 356/446 |
| 4,468,117 | 8/1984 | Hortouni et al. | 356/73.1 |
| 4,580,552 | 4/1986 | Nishioki et al. | 350/96.26 X |
| 4,615,582 | 10/1986 | Lefevre et al. | 350/96.15 X |
| 4,732,474 | 3/1988 | Chikama | 356/446 |
| 4,737,035 | 4/1988 | Aoki et al. | 356/446 |

FOREIGN PATENT DOCUMENTS

| | | | |
|---|---|---|---|
| 32774 | 7/1981 | European Pat. Off. | 356/446 |
| 1959612 | 6/1971 | Fed. Rep. of Germany | 356/446 |
| 0068495 | 6/1977 | Japan | 356/445 |
| 0216241 | 10/1985 | Japan | 356/73.1 |

Primary Examiner—Richard A. Rosenberger
Attorney, Agent, or Firm—Sughrue, Mion, Zinn, Macpeak & Seas

[57] ABSTRACT

A reflection density measuring system comprises an incubator in which a plurality of chemical assay slides can be accommodated and arranged in one plane, a light source disposed outside the incubator, and a measuring head connected to the light source by way of a fiber optic member. The measuring head is movable to be opposed to each of the chemical assay slides in the incubator under deformation of the fiber optic member, and the fiber optic member is formed of an optical fiber bundle at least at the portion at which the fiber optic member is deformed in response to movement of the measuring head.

12 Claims, 2 Drawing Sheets

REFLECTION DENSITY MEASURING SYSTEM

BACKGROUND OF THE INVENTION

1. Field of the Invention

This invention relates to a reflection density measuring system in which light is projected onto a surface whose reflection density is to be measured and reflected light from the surface is received by a photodetector, whereby the reflection density of the surface is measured.

2. Description of the Prior Art

There has been put into practice a dry-type chemical assay slide for quantitative analysis of a particular component contained in a droplet of a sample liquid such as blood or urine. See Japanese Patent Publication No. 53(1978)-21677, Japanese Unexamined Patent Publication No. 55(1980)-164356 or the like.

When analyzing chemical components in a sample liquid using such a chemical assay slide, a droplet of the sample liquid is deposited on the slide and is held at a constant temperature for a predetermined time in an incubator to permit coloring reaction, and the optical density of the color formed by the coloring reaction is optically measured. That is, measuring light containing a wavelength selected in advance according to the combination of the component to be measured in the sample liquid and the reagent contained in the reagent layer of the slide is projected onto the chemical assay slide and the optical density of the reflected light is measured. Then the content of the component to be measured is quantified on the basis of the optical density of the reflected light by colorimetry.

The optical density of the reflected light is measured by a reflection density measuring system. The reflection density measuring system generally comprises an incubator for receiving the chemical assay slide, and a measuring head which can be opposed to the surface-to-be-measured of the slide in the incubator. After the chemical assay slide is incubated in the incubator, the measuring head is opposed to the surface-to-be-measured of the slide and light is projected onto the surface-to-be-measured by the head and reflected light from the surface-to-be-measured is received by a photosensor in the head.

In medical facilities, laboratories and the like where numerous samples are analized, it is preferred that the reflection densities of a plurality of samples can be sequentially measured, and accordingly there have been proposed various systems for sequentially effecting measurement of reflection densities of a plurality of samples.

For example, in the system disclosed in Japanese Unexamined Patent Publication No. 56(1981)-77746, a plurality of chemical assay slides are sandwiched between a pair of rotatable disks spaced from each other at regular intervals in the circumferential direction of the disks and held at a constant temperature by an incubating heater means provided on the disks, and after incubation for a predetermined time interval, the disks are rotated to successively bring the chemical assay slides into alignment with a measuring head disposed below the disks. Then irradiation light is projected onto each chemical assay slide by the measuring head through an opening formed in the lower disk and reflected light is detected by a photosensor. However, the system is disadvantageous in that complicated and cumbersome rotating system and controlling systems are necessary for rotating the large and heavy disks, thereby adding to the overall size of the system and manufacturing cost.

SUMMARY OF THE INVENTION

In view of the foregoing observations described, the primary object of the present invention is to provide a reflection density measuring system which is adapted to sequentially measure the reflection densities of a plurality of samples and is simple in structure.

In accordance with one aspect of the present invention, the reflection density measuring system comprises an incubator in which a plurality of chemical assay slides can be accommodated and arranged in one plane, a light source disposed outside the incubator, and a measuring head connected to the light source by way of an optical fiber bundle, the measuring head being movable to be opposed to each of the chemical assay slides in the incubator under deformation of the optical fiber bundle.

In the reflection density measuring system, the measuring head can be small both in size and weight since it is separated from the light source, and is moveable. Further, since the measuring head is connected with the light source by way of an optical fiber bundle, a constant amount of irradiating light can be projected onto the chemical assay slides even if the measuring head is moved from slide to slide. That is, if a single optical fiber having a relatively large thickness is used in order to sufficiently transmit light emitted from the light source to the measuring head, a large amount of light will be lost when the optical fiber is bent. On the other hand, in the case of an optical fiber bundle formed by bundling a plurality of thin optical fibers, loss of light due to bending of the bundle is minimized, and accordingly, the amount of light irradiated from the measuring head does not fluctuate even if the measuring head is moved under deformation of the fiber bundle. By thus moving the measuring head with respect to the incubator instead of moving the incubator with the respect to the measuring head, a plurality of chemical assay slides can be continuously analyzed with a simple structure.

In accordance with another aspect of the present invention, the reflection density measuring system comprises an incubator in which a plurality of chemical assay slides can be accommodated and arranged in one plane, a light source disposed outside the incubator, and a measuring head connected to the light source by way of a fiber optic means, the measuring head being movable to be opposed to each of the chemical assay slides in the incubator under deformation of the fiber optic means, the portion of the fiber optic means at which the fiber optic means is deformed upon movement of the measuring head being formed of an optical fiber bundle and the portion of the fiber optic means directly connected to the measuring head being formed of a single optical fiber.

In this system, since the portion of the fiber optic means at which the fiber optic means is deformed or bent due to movement of the measuring head is formed of an optical fiber bundle, loss of light at the bend of the fiber optic means is minimized, and at the same time, since the portion of the fiber optic means directly connected to the measuring head is formed of a single fiber, fluctuation in light distribution on the surface-to-be-determined of the chemical assay slides is minimized. This is advantageous because when the fiber optic means is formed of an optical fiber bundle at the portion directly connected to the measuring head, the irradiation light from the light source emanates from each of the fine optical fibers at the emanating end of the fiber optic means to cause fluctuation in light distribution on the surface-to-be-measured.

DESCRIPTION OF THE PREFERRED EMBODIMENTS

Figure 1:
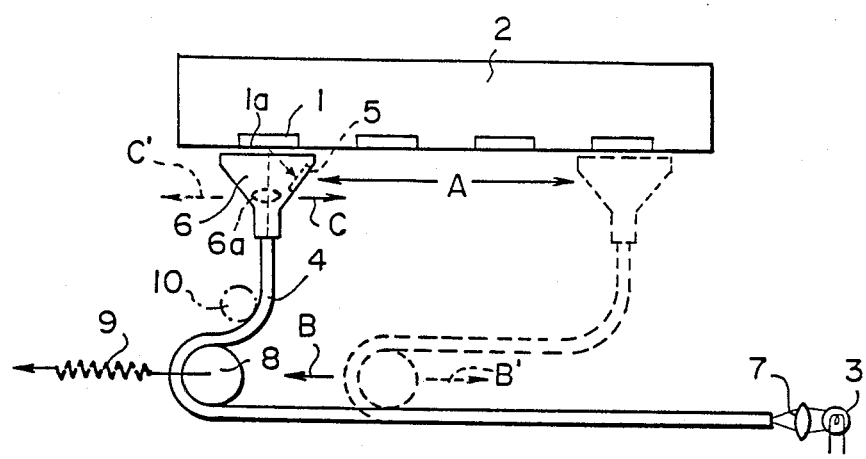
FIG. 1 is a schematic side view showing a reflection density measuring system in accordance with an embodiment of the present invention.

In FIG. 1, a reflection density measuring system in accordance with an embodiment of the present invention comprises an incubator 2 in which four chemical assay slides 1 can be accommodated in one plane, a light source 3, e.g., a halogen lamp, which is fixedly disposed in a predetermined position outside the incubator 2 and emits an irradiation light suitable for measuring the reflection density of the surfce-to-be-measured 1a of each slide 1, and a measuring head 6 connected to the light source 3 by way of an optical fiber bundle 4. The measuring head 6 is provided with a photosensor 5 which may be a silicon photodiode. The irradiated light emitted from the light source 3 is transmitted through the optical fiber bundle 4 to impinge upon the surface-to-be-measured 1a and the light reflected at the surface 1a is received by the photosensor 5. Reference numeral 7 denotes a condenser lens for efficiently introducing the irradiated light emitted from the light source 3 into the optical fiber bundle 4. A lens 6a in the measuring head 6 converges the irradiated light emanating from the optical fiber bundle 4 into a beam having a desired diameter on the surface-to-be-measured 1a.

The measuring head 6 is movable and can be opposed to each of the chemical assay slides 1 in the incubator 2 under deformation of the optical fiber bundle 4. That is, the measuring head 6 is moved between the position shown by the solid line in FIG. 1 and the position shown by the broken line as indicated by arrows A. The movement of the measuring head 6 will be described hereinbelow.

Figure 2:
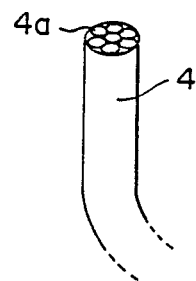
FIG. 2 is an enlarged fragmentary perspective view showing the optical fiber bundle employed in the system of the embodiment.

The measuring head 6 receives the irradiated light emitted from the light source 3 by way of the optical fiber bundle 4, and is smaller in size and weight than a measuring head having a built-in light source, and accordingly, is more adapted to movement. Further, since the optical fiber bundle 4 formed by bundling a plurality of thin optical fibers 4a as shown in FIG. 2 is used for transmitting the irradiated light to the measuring head 6, loss of the irradiated light due to bending is little.

However, since the radius of curvature of the optical fiber bundle 4 can affect the light transmission efficiency of the optical fiber bundle 4 to adversely affect the measuring accuracy, it is preferred that the optical fiber bundle 4 be arranged so that the radius of curvature of the bent portion is constant irrespective of the position of the measuring head 6. In this particular embodiment, the optical fiber bundle 4 is passed around a rotatable pulley 8 which is urged in the direction of arrow B by a spring 9. The measuring head 6 is moved in the direction of arrow C or C' by a driving means (not shown) to be opposed to each of the slides 1 in the incubator 2. By virtue of the pulley 8, the radius of curvature of the bent portion of the optical fiber bundle 4 is kept equal to the radius of the pulley 8 irrespective of the position of the measuring head 6.

If desired, a circular support member 10 having a predetermined diameter may be provided to abut against the optical fiber bundle 4 from the side opposite to the pulley 8, as shown by the chained line, so that the radius of curvature of the upwardly bent portion of the optical fiber bundle 4 is also kept constant irrespective of the position of the measuring head 6. The support member 10 is arranged to be moved in response to movement of the measuring head 6.

Figure 3:
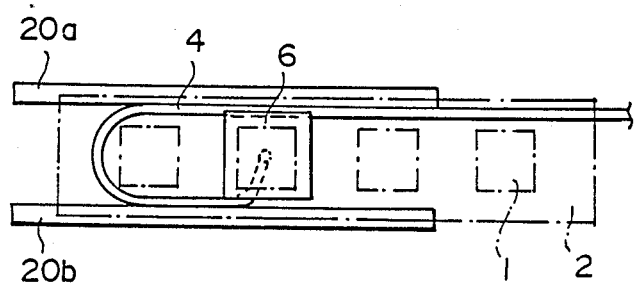
FIG. 3 is a schematic plan view illustrating another embodiment of the present invention.

As the means for keeping the radius of curvature of the bent portion of the optical fiber bundle 4 constant, a pair of guide plates 20a and 20b provided to abut against the optical fiber bundle 4 on opposite sides of the bent portion thereof as shown in FIG. 3 may be used instead of the pulley 8.

Figure 4:
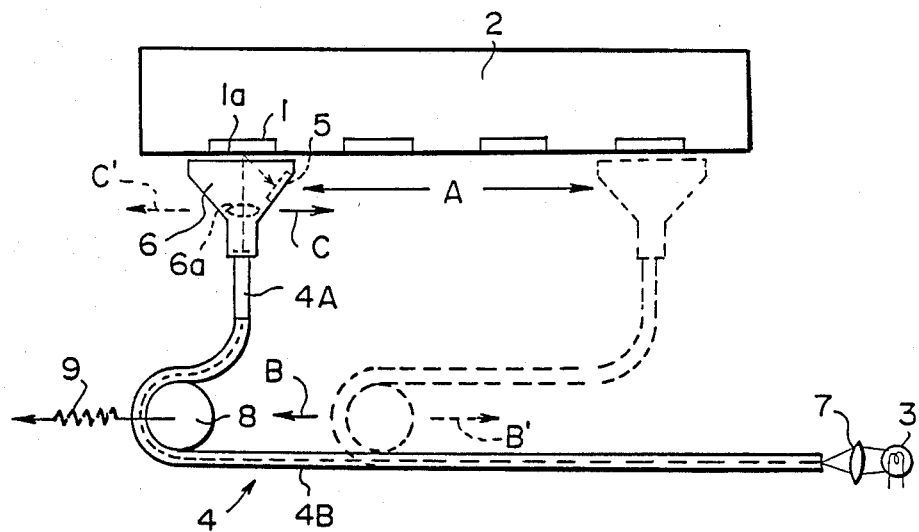
FIG. 4 is a view similar to FIG. 1 but showing still another embodiment of the present invention.

Now another embodiment of the present invention will be described with reference to FIG. 4. The reflection density measuring system of this embodiment is very similar to that shown in FIG. 1 and accordingly, in FIG. 4, the parts analogous to the parts shown in FIG. 1 are given the same reference numerals and will not be described here. The only difference between the systems shown in FIGS. 1 and 4 is that, in the latter system, the measuring head 6 is connected with the light source 3 by way of a fiber optic member 4 comprising a single optical fiber portion 4A and an optical fiber bundle portion 4B. The single optical fiber portion 4A includes at least the emanating end portion of the fiber optic member 4 and the optical fiber bundle portion 4B forms at the least the portion at which the fiber optic member 4 is deformed in response to movement of the measuring head 6. The portions of the fiber optic member 4 other than the emanating end portion and the portion at which the fibre optic member 4 is deformed may be either of a single optical fiber or an optical fiber bundle. As described above, by forming the portion at which the fiber optic member 4 is deformed by an optical fiber bundle, loss of light at the bent portion of the fiber optic member 4 is minimized.

Figure 5:
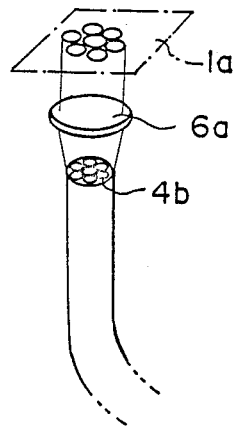
FIG. 5 is a view for illustrating an effect of the embodiment shown in FIG. 4.

When the whole of the fiber optic member 4 is of an optical fiber bundle as shown in FIG. 5, unevenness in light intensity distribution is produced on the surface-to-be-measured corresponding to the emanating ends of the thin optical fibers 4b forming the optical fiber bundle. This the reason why the emanating end portion of the fiber optic member 4 is formed of the single optical fiber portion 4A.

It is preferred that a Selfock lens be inserted between the single optical fiber portion 4A and the optical fiber bundle portion 4B in order to minimize loss of light at the junction thereof.

The number of the chemical slides 1 to be accommodated in the incubator 2, the arrangement of the slides 1 and the like need not be limited those employed in the above embodiments. Further, the direction of the movement of the measuring head and the means for deforming the fiber optic member need not be limited to those described above but may be freely selected as desired.

We claim:

1. A reflection density measuring system for measuring the reflection density of a plurality of objects each having a surface-to-be-measured and being arranged in a common plane on a support means, said system comprising: a light source disposed outside the support means, a measuring head connected to the light source through an optical fiber bundle, the measuring head being movable, under deformation of the optical fiber bundle, to measuring positions which oppose a respective object, the measuring head having a photosensor which receives light which is emitted from the light source and which is subsequently reflected at the surface-to-be-measured, thereby measuring the reflection density of the surface-to-be-measured, said system further comprising means for keeping constant the radius of curvature of the bent portion of the optical fiber bundle in any measuring position of the measuring head.

2. The reflection measuring density system of claim 1, wherein the support means comprises an incubator.

3. The reflection density measuring system of claim 1, wherein said maintaining means comprises a pair of guide plates disposed to abut against the optical fiber bundle on opposite sides of the bent portion thereof.

4. The reflection density measuring system of claim 1, wherein said maintaining means comprises a rotatable pulley, and means for urging said rotatable pulley in a direction opposite to the direction of movement of the measuring head.

5. The reflection density measuring system of claim 4, further comprising circular support means, having a predetermined diameter, for abutting against the optical fiber bundle from a side opposite to said rotatable pulley, said circular support means being movable in response to the movement of the measuring head.

6. A reflection density measuring system as defined in claim 1, wherein said objects are chemical assay slides.

7. A reflection density measuring system for measuring the reflection density of a plurality of objects each having a surface-to-be-measured and being arranged in a common plane on a support means, said system comprising: a light source disposed outside the support means, a measuring head connected to the light source through a fiber optic means, the measuring head being movable, under deformation of the fiber optic means, to measuring positions which oppose a respective object, the portion of the fiber optic means at which the fiber optic means is deformed upon movement of the measuring head being formed of an optical fiber bundle and the emanating end portion of the fiber optic means which is directly connected to the measuring head being formed of a single optical fiber, and the measuring head being provided with a photosensor which receives light which is emitted from the light source and which is subsequently reflected at the surface-to-be-measured, thereby measuring the reflection density of the surface-to-be-measured, said system further comprising means for keeping constant the radius of curvature of the bent portion of the fiber optic means at all measuring positions of the measuring head.

8. The reflection measuring density system of claim 7, wherein the support means comprises an incubator.

9. The reflection density measuring system of claim 7, wherein said maintaining means comprises a pair of guide plates disposed to abut against the fiber optic means on opposite sides of the bent portion thereof.

10. The reflection density measuring system of claim 7, wherein said maintaining means comprises a rotatable pulley, means for urging said rotatable pulley in a direction opposite to the direction of movement of the measuring head.

11. The reflection density measuring system of claim 10, further comprising circular support means, having a predetermined diameter, for abutting against the fiber optic means from a side opposite to said rotatable pulley, said circular support means being movable in response to the movement of the measuring head.

12. A reflection density measuring system as defined in claim 4, wherein said objects are chemical assay slides.

* * * * *